United States Patent
Phalen et al.

(10) Patent No.: US 7,294,125 B2
(45) Date of Patent: Nov. 13, 2007

(54) METHODS OF DELIVERING ENERGY TO BODY PORTIONS TO PRODUCE A THERAPEUTIC RESPONSE

(75) Inventors: Michael P. Phalen, Shrewsbury, MA (US); Stephen F. Moreci, Hopedale, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 431 days.

(21) Appl. No.: 10/887,324

(22) Filed: Jul. 9, 2004

(65) Prior Publication Data

US 2005/0055053 A1    Mar. 10, 2005

Related U.S. Application Data

(60) Provisional application No. 60/496,926, filed on Aug. 22, 2003.

(51) Int. Cl.
*A61N 7/00* (2006.01)
(52) U.S. Cl. ............................................. 606/27; 601/2
(58) Field of Classification Search ................ 600/459, 600/462; 601/2; 606/27–31
See application file for complete search history.

(56) References Cited

U.S. PATENT DOCUMENTS

| | | | |
|---|---|---|---|
| 6,063,085 A | 5/2000 | Tay et al. | |
| 6,156,032 A | 12/2000 | Lennox | |
| 6,409,723 B1 * | 6/2002 | Edwards | 606/41 |
| 6,635,054 B2 | 10/2003 | Fjield et al. | |
| 6,740,082 B2 | 5/2004 | Shadduck | |
| 2001/0031922 A1 | 10/2001 | Weng et al. | |
| 2002/0133148 A1 | 9/2002 | Daniel et al. | |
| 2004/0082859 A1 * | 4/2004 | Schaer | 600/459 |

OTHER PUBLICATIONS

Boston Scientific forms ties to Therus, *Boston Business Journal*, May 2, 2002 (2 pages). http://boston.bizjournals.com/boston/stories/2002/04/29/daily45.html.

Ablatherm: High Intensity Focused Ultrasound Treatment for Localized Prostate Cancer: Patient Information, *Patient Brochure issued by EDAP—The HIFU Company*, Jul. 2003 (16 pages).

Therus Theraseal, *Graphical Renderings of Product Prototypes developed by the Stratos Product Development Group*, Aug. 10, 2003 (3 pages). http://www.stratos.com/HTML/work/therus-theraseal.shtml.

About Therus, *Therus Corporation*, Aug. 10, 2003 (1 page). http://www.therus.com/about.html.

Clinical Applications, *Therus Corporation*, Aug. 10, 2003 (1 page). http://www.therus.com/clinical_apps.html.

(Continued)

*Primary Examiner*—Roy D. Gibson
(74) *Attorney, Agent, or Firm*—Finnegan, Henderson, Farabow, Garrett & Dunner L.L.P.

(57) ABSTRACT

The invention relates to methods of applying energy to various body portions to produce a therapeutic response. According to embodiments, the applied energy is ultrasound and may be delivered by an ultrasound focusing device deployed in the body, for example, by using an endoscope. The energy may be used to effect a variety of therapeutic responses, including ablating lesions in the gall bladder, treating gastrointestinal reflux disease, or treating fecal incontinence.

27 Claims, 7 Drawing Sheets

OTHER PUBLICATIONS

Leslie, Mitch, Inside-Out Ultrasound: A New Way to View the Digestive System, *Stanford Medicine*, vol. 18, No. 1, Winter/Spring 2001. http://www.med.stanford.edu/center/communications/stanmed/2001winterspring/ultrasoud.html.

Ablatherm: EDAP—Prostate Cancer treated by HIFU, High Intensity Focused Ultrasound: Homepage, *Website of EDAP—The HIFU Company*, Jul. 9, 2004 (1 page). http://www.edap-hifu.com.

Prostate Cancer Curative Treatments—EDAP-HIFU: What are the Curative Treatments for Prostate Cancer?, *Website of EDAP—The HIFU Company*, Jul. 9, 2004 (2 pages). http://www.edap-hifu.com/eng/patients/prostate_cancer/1f_info_curative_treat.htm.

Prostate Cancer Tretments With Ablatherm—EDAP-HIFU: Quick Overview of the HIFU—Ablatherm Therapy, *Website of EDAP—The HIFU Company*, Jul. 9, 2004 (2 pages). http://www.edap-hifu.com/eng/patients/prostate_cancer/2a_hifu_overview.htm.

HIFU Treatment With Ablatherm—History—EDAP-HIFU: How, When and Where did it Start!, *Website of EDAP—The HIFU Company*, Jul. 9, 2004 (1 page). http://www.edap-hifu.com/eng/patients/prostate_cancer/2b_hifu_history.htm.

Prostate Cancer Treatment With Ablatherm—EDAP-HIFU: What is Ablatherm?, *Website of EDAP—The HIFU Company*, Jul. 9, 2004 (2 pages). http://www.edap-hifu.com/eng/patients/prostate_cancer/2c_hifu_whatis.htm.

Prostate Cancer Treatments With Ablatherm—EDAP-HIFU: How is Ablatherm Treatment Performed?, *Website of EDAP—The HIFU Company*, Jul. 9, 2004 (3 pages). http://www.edap-hifu.com/eng/patients/prostate_cancer/2d_hifu_treatment.htm.

Prostate Cancer Treatments With Ablatherm—EDAP-HIFU: What Happens After the Treatment?, *Website of EDAP—The HIFU Company*, Jul. 9, 2004 (2 pages). http://www.edap-hifu.com/eng/patients/prostate_cancer/2e_hifu_followup.htm.

Prostate Cancer Treatments With Ablatherm—EDAP-HIFU: What Results Could You Expect?, *Website of EDAP—The HIFU Company*, Jul. 9, 2004 (1 page). http://www.edap-hifu.com/eng/patients/prostate_cancer/2f_hifu_results.htm.

Prostate Cancer Treatments With Ablatherm—EDAP-HIFU: What Are Possible Side Effects?, *Website of EDAP—The HIFU Company*, Jul. 9, 2004 (2 pages). http://www.edap-hifu.com/eng/patients/prostate_cancer/2g_hifu_sideeffects.htm.

Prostate Cancer Treatments With Ablatherm—EDAP-HIFU: What are the Benefits and Goals?, *Website of EDAP—The HIFU Company*, Jul. 9, 2004 (1 page). http://www.edap-hifu.com/eng/patients/prostate_cancer/2h_hifu_benefits.htm.

Prostate Contact Treatment Clinical Trial—EDAP-HIFU, *Website of EDAP—The HIFU Company*, Jul. 9, 2004 (2 pages). http://www.edap-hifu.com/eng/patients/prostate_cancer/3_clinical_trial_europe.htm.

Prostate Cancer Treatment with Focalised Ultrasound—EDAP-HIFU: Frequently Asked Questions, *Website of EDAP—The HIFU Company*, Jul. 9, 2004 (2 pages). http://www.edap-hifu.com/eng/patients/prostate_cancer/5_FAQ.htm.

EDAP: Prostate Cancer Treated by HIFU, High Intensity Focused Ultrasound: Headlines, *Website of EDAP—The HIFU Company*, Jul. 9, 2004 (2 pages). http://www.edap-hifu.com/eng/physicians/news/index.htm.

Prostate Cancer Treated by HIFU, High Intensity Focused Ultrasound: Mainpage, *Website of EDAP—The HIFU Company*, Jul. 9, 2004 (3 pages). http://www.edap-hifu.com/eng/physicians/hifu/index.htm.

Prostate Cancer Treated by HIFU, High Intensity Focused Ultrasound, Principles: What is HIFU?, *Website of EDAP—The HIFU Company*, Jul. 9, 2004 (1 page). http://www.edap-hifu.com/eng/physicians/hifu/2a_hifu_overview.htm.

Prostate Cancer Treated by HIFU, High Intensity Focused Ultrasound, Principles: History: How, When and Where Did It Start?, *Website of EDAP—The HIFU Company*, Jul. 9, 2004 (2 pages). http://www.edap-hifu.com/eng/physicians/hifu/2b_hifu_history.htm.

Prostate Cancer Treated by HIFU, High Intensity Focused Ultrasound, Principles: What are the Physical Principles?, *Website of EDAP—The HIFU Company*, Jul. 9, 2004 (2 pages). http://www.edap-hifu.com/eng/physicians/hifu/2c_physical.htm.

Prostate Cancer Treated by HIFU, High Intensity Focused Ultrasound, Principles: How Does HIFU Create a Lesion?, *Website of EDAP—The HIFU Company*, Jul. 9, 2004 (1 page). http://www.edap-hifu.com/eng/physicians/hifu/2d_hifu_lesion.htm.

Prostate Cancer Treated by HIFU, Ablatherm: Overview of HIFU Treatment With Ablatherm, *Website of EDAP—The HIFU Company*, Jul. 9, 2004 (2 pages). http://www.edap-hifu.com/eng/physicians/hifu/3a_treatment_overview.htm.

Prostate Cancer Treated by HIFU, Ablatherm: A Brief History of Ablatherm Development, *Website of EDAP—The HIFU Company*, Jul. 9, 2004 (1 page). http://www.edap-hifu.com/eng/physicians/hifu/3b_treatment_history.htm.

Prostate Cancer Treated by HIFU, Ablatherm: How is Ablatherm Treatment Performed?, *Website of EDAP—The HIFU Company*, Jul. 9, 2004 (3 pages). http://www.edap-hifu.com/eng/physicians/hifu/3c_treatment_treat-description.htm.

Prostate Cancer Treated by HIFU, Ablatherm: What Kind of Follow-up After Ablatherm?, *Website of EDAP—The HIFU Company*, Jul. 9, 2004 (1 page). http://www.edap-hifu.com/eng/physicians/hifu/3d_treatment_followup.htm.

Prostate Cancer Treated by HIFU, Ablatherm, Clinical Information: Histological Changes After Ablatherm, *Website of EDAP—The HIFU Company*, Jul. 9, 2004 (1 page). http://www.edap-hifu.com/eng/physicians/hifu/4b_info_histology.htm.

Prostate Cancer Treated by HIFU, Ablatherm, Clinical Information: MRI Post Treatment, *Website of EDAP—The HIFU Company*, Jul. 9, 2004 (1 page). http://www.edap-hifu.com/eng/physicians/hifu/4c_info_mri.htm.

Prostate Cancer Treated by HIFU, Ablatherm, Clinical Information: PSA Evolution Post Treatment, *Website of EDAP—The HIFU Company*, Jul. 9, 2004 (2 pages). http://www.edap-hifu.com/eng/physicians/hifu/4d_info_psa.htm.

Prostate Cancer Treated by HIFU, Ablatherm, Clinical Result: Large Cohort Studies, *Website of EDAP—The HIFU Company*, Jul. 9, 2004 (2 pages). http://www.edap-hifu.com/eng/physicians/hifu/5a_results_standard.htm.

Prostate Cancer Treated by HIFU, Ablatherm, Clinical Result: Long Term Results, *Website of EDAP—The HIFU Company*, Jul. 9, 2004 (2 pages). http://www.edap-hifu.com/eng/physicians/hifu/5b_results_longterm.htm.

Prostate Cancer Treated by HIFU, Ablatherm, Clinical Result: PSA Stability, *Website of EDAP—The HIFU Company*, Jul. 9, 2004 (1 page). http://www.edap-hifu.com/eng/physicians/hifu/5c_results_psa.htm.

Prostate Cancer Treated by HIFU, Ablatherm, Clinical Result: Safety Results, *Website of EDAP—The HIFU Company*, Jul. 9, 2004 (1 page). http://www.edap-hifu.com/eng/physicians/hifu/5c_results_safety.htm.

Prostate Cancer Treated by HIFU, Ablatherm, Clinical Trials: Europe, *Website of EDAP—The HIFU Company*, Jul. 9, 2004 (2 pages). http://www.edap-hifu.com/eng/physicians/hifu/6_trials_europe.htm.

Prostate Cancer Treated by HIFU, Ablatherm, Published Articles, Abstracts, *Website of EDAP—The HIFU Company*, Jul. 9, 2004 (11 pages). http://www.edap-hifu.com/eng/physicians/hifu/7_published.htm.

* cited by examiner

METHODS OF DELIVERING ENERGY TO BODY PORTIONS TO PRODUCE A THERAPEUTIC RESPONSE

CROSS-REFERENCE TO RELATED APPLICATIONS

This patent application claims the benefits of priority under 35 U.S.C. §§119, 120 to U.S. Provisional Patent Application No. 60/496,926, entitled METHODS OF DELIVERING ENERGY TO BODY PORTIONS TO PRODUCE A THERAPEUTIC RESPONSE, filed on Aug. 22, 2003, the entirety of which is incorporated herein by reference.

DESCRIPTION OF THE INVENTION

1. Field of the Invention

The invention relates to methods of applying energy to various body portions to produce a therapeutic response. According to embodiments, the applied energy is ultrasound and may be delivered by an ultrasound focusing device deployed in the body, for example, by using an endoscope. The energy may be used to effect a variety of therapeutic responses, including ablating lesions in the gall bladder or other organs, treating gastrointestinal reflux disease, or treating fecal incontinence.

2. Background of the Invention

Minimizing the invasiveness of medical procedures is desirable. Generally, more invasive procedures are more expensive and result in more complications and more discomfort to the patient. For example, open surgery is an invasive medical procedure with significant attendant risks. Due to relatively large incisions necessary in the performance of open surgery, relatively large amounts of blood may be lost, the risk of infection increases, and the potential for post-operative hernias is high. Further, the relatively large incisions necessary in the performance of open surgery require extended recovery times for the incisions to heal.

Laparoscopic procedures are less invasive than open surgery. Laparoscopic procedures often involve performing laparotomies for trocar ports (penetrations of the abdominal walls), percutaneous endoscopic gastronomies (incisions through the skin into the various bodily organs), and the installation of ports through which medical devices are inserted. This procedure also requires incisions through, for example, the abdominal walls, risking infection. The location of the incision in the bodily wall also presents a risk of other negative effects, such as sepsis, which can be caused by leakage of septic fluid contained in the stomach.

Medical treatments that would benefit from less invasive procedures include, for example, vascular sealing, ablating lesions in the gall bladder or other body organs, treatment of gastrointestinal reflux disease, or treatment of fecal incontinence, among others.

Vascular sealing is often necessary in medical procedures that access the vascular system of the patient. Although various means may be used to obtain access into a vein or artery, typically access is obtained by inserting a cannula or introducer sheath through the skin and into the selected blood vessel. A medical device or diagnostic instrument, such as a guide wire, guiding catheter, balloon angioplasty device, atherectomy device, or the like, then is inserted into the vascular system through the cannula or introducer sheath.

To permit the insertion of a medical device or instrument therethrough, the introducer sheath must be of a relatively large diameter. Introducer sheaths typically have a diameter in the range between one millimeter and six millimeters, thus creating a significant puncture in the blood vessel, such as a puncture 17 into a vessel 10 as shown in FIGS. 1A and 1B. After the intravascular medical procedure is completed, puncture 17 must be closed and bleeding from the blood vessel 10 stopped. In the examples shown in FIGS. 1A and 1B, the puncture 17 goes through the subcutaneous tissue 13, the vascular sheath 12, and the vessel wall 11. The vessel wall includes the adventitia 16, media layer 15, and intima layer 14, as shown in FIGS. 1C and 1D.

At present, bleeding may be stopped by the application of direct digital pressure over the puncture by a trained physician or other suitably trained medical personnel. Such direct pressure must be applied for a sufficiently long time for hemostasis to occur so that the puncture is effectively closed and further bleeding is prevented. In the case of punctures into the femoral artery, the pressure is generally applied for twenty to thirty minutes, but it may be necessary to apply pressure for longer and/or through other devices that apply pressure.

Stopping bleeding using digital pressure is not an efficient use of medical professional services. The procedure also results in a substantial reduction, if not virtual arrest, of blood flow through the vessel. Since thrombosis is one of the major problems that can occur in the immediate post-operative period, reduction in blood flow caused by the application of digital pressure is undesirable. Furthermore, when digital pressure is applied, an undesirable bruise or hematoma can form at the entry site, since internal bleeding of the punctured artery continues until clotting blocks the puncture. There is also a risk that upon movement by the patient, the puncture will reopen and begin bleeding again, resulting in a hematoma or other complications. In addition, when anticoagulants used in the medical procedure are left active in the body, the introducer sheath is generally left inside the patient for a relatively long period of time in order for the anticoagulants to clear from the blood. Because the patient may be required to remain immobile and because of the risk of complications, patients are usually required to remain overnight in the hospital for observation, increasing the cost of the overall procedure.

Devices exist to effect vascular sealing. Once such device is an expandable plug pushed through the puncture into the blood vessel and into the blood stream. Once exposed to blood, the plug expands. The expanded plug is then pulled back against the puncture where, because of its expanded size, it plugs the opening. A similar device is an expandable closure. Such devices may work satisfactorily, but require inserting and leaving a foreign object in the vessel for a period of time. It is usually medically preferable to avoid leaving objects in a vessel, even if they eventually biodegrade.

Ablating portions of a gall bladder, or other bodily organs, is sometimes necessary to treat and/or destroy cancerous or noncancerous lesions that may exist on the surface or in the interior of the gall bladder, such as a lesion 51 in gall bladder 50 shown in FIG. 2. Removal of these lesions is desirable to prevent them from spreading and/or infecting additional portions of the gall bladder, as even lesions in a noncancerous form may interfere with the proper functioning of the gall bladder.

Current methods of removing such lesions include open surgery where the lesion is either cut away from the surface of the gall bladder, or if the lesion is on the interior of the gall bladder, the gall bladder is cut open to gain access to the interior of the gall bladder, at which point the lesion is removed. Laparoscopic methods of removing a lesion also exist where a removal device is inserted through the abdominal wall and into the gall bladder to remove the lesion. However, the attendant complications that accompany open surgery and laparoscopic procedures are present in these cases, and are particularly relevant where the lesions are on the interior portion of the gall bladder. Accordingly, a less invasive method of removing such lesions is desired.

Gastroesophageal reflux occurs when stomach acid enters the esophagus from the stomach. (See a portion of the gastrointestinal tract, as shown in FIGS. 3A and 3B, that depicts esophagus 33 and stomach 30). This reflux of acid into the esophagus occurs naturally in healthy individuals, but also may become a pathological condition in others. Effects from gastroesophageal reflux range from mild to severe. Mild effects include heartburn, a burning sensation experienced behind the breastbone. More severe effects include a variety of complications, such as esophageal erosion, esophageal ulcers, esophageal stricture, abnormal epithelium (e.g., Barrett's esophagus), and/or pulmonary aspiration. These various clinical conditions and changes in tissue structure that result from reflux of stomach acid from the stomach into the esophagus are referred to generally as Gastroesophageal Reflux Disease (GERD).

Many mechanisms contribute to prevent gastroesophageal reflux in healthy individuals. One such mechanism is the functioning of the lower esophageal sphincter (LES), shown as element 34 in FIGS. 3A and 3B. The LES is a ring of smooth muscle and increased annular thickness existing in approximately the last four centimeters of the esophagus. In its resting state, the LES creates a region of high pressure (approximately 15-30 mm Hg above intragastric pressure) at the opening of the esophagus into the stomach. This pressure essentially closes the esophagus so that contents of the stomach cannot pass back into the esophagus. The LES opens in response to swallowing and peristaltic motion in the esophagus, allowing food to pass into the stomach. After opening, however, a properly functioning LES should return to the resting, or closed state. Transient relaxations of the LES do occur in healthy individuals, typically resulting in occasional bouts of heartburn.

The physical interaction occurring between the gastric fundus and the esophagus also prevents gastroesophageal reflux. The gastric fundus, shown as element 35 in FIGS. 3A and 3B, is a lobe of the stomach situated at the top of the stomach distal to the esophagus. In asymptomatic individuals, the fundus presses against the opening of the esophagus when the stomach is full of food and/or gas. This effectively closes off the esophageal opening to the stomach and helps to prevent acid reflux back into the esophagus. More specifically, as the food bolus is immersed in gastric acid, it releases gas which causes the fundus of the stomach to expand and thereby exert pressure on the distal esophagus causing it to collapse. The collapse of the esophagus lumen reduces the space for the stomach acid to splash past the closed esophagus lumen and thereby protect the proximal esophagus from its destructive contact.

In individuals with GERD, the LES functions abnormally, either due to an increase in transient LES relaxations, decreased muscle tone of the LES during resting, or an inability of the esophageal tissue to resist injury or repair itself after injury. These conditions often are exacerbated by overeating, intake of caffeine, chocolate or fatty foods, smoking, and/or hiatal hernia. Avoiding these exacerbating mechanisms helps curb the negative side effects associated with GERD, but does not change the underlying disease mechanism. Accordingly, some type of medical treatment is often necessary to correct, or at least improve, this condition.

A surgical procedure, known generally as fundoplication, has been developed to prevent acid reflux in patients whose normal LES functioning has been impaired, either as a result of GERD or other adverse effects. This procedure involves bringing the fundus wall into closer proximity of the esophageal wall to help close off the esophageal opening into the stomach. Traditionally, this procedure has been performed as an open surgery, but also has been performed laparoscopically. As with any surgery or laparoscopic procedure, however, fundoplication involves certain attendant risks. Thus, an alternative, minimally invasive technique is preferable.

Fecal incontinence, which is most common in the elderly, is the loss of voluntary control to retain stool in the rectum, shown as element 40 in FIGS. 4A and 4B. In most cases, fecal incontinence is the result of an impaired involuntary internal anal sphincter 41. The internal sphincter may be incompetent due to laxity or discontinuity. Discontinuity, or disruption of the internal anal sphincter, can be caused by a number of different muscle injuries.

In most patients, fecal incontinence is initially treated with conservative measures, such as biofeedback training or alteration of the stool consistency. Biofeedback is successful in approximately two-thirds of patients who retain some degree of rectal sensation and functioning of the external anal sphincter 42. However, multiple sessions are often necessary, and patients need to be highly motivated. Electronic home biofeedback systems are available and may be helpful as adjunctive therapy.

Several surgical approaches to fecal incontinence have been tried, with varying success, when conservative management has failed. These treatments include sphincter repair, gracilis or gluteus muscle transposition to reconstruct an artificial sphincter, and colostomy. The approach that is used depends on the cause of the incontinence and the expertise of the surgeon. However, the attendant risks associated with there surgical approaches are still present. Accordingly, a less invasive medical procedure for treating fecal incontinence is desired.

Patients may have mechanical devices implanted in their body, for example, to treat cancer, or mechanical devices placed in the body to perform a treatment. Examples of mechanical devices that may be implanted in the body or placed in the body to perform a treatment include stents, grafts, needles, and knives. Some of these mechanical devices may, once implanted or placed in the body, require activation. One method of activating these mechanical devices is to run a wire from the mechanical device to the exterior of the patient's body, and then apply energy to the mechanical device through the wire. However, running wires through the body for prolonged periods of time are especially undesirable as it may lead to medical complications such as internal hemorrhaging. Accordingly, a less invasive way of activating the mechanical devices is desired.

SUMMARY OF THE INVENTION

In accordance with the invention, an embodiment of the invention includes a method of. treating a patient with gastrointestinal reflux disease by applying energy to an esophageal sphincter to produce a therapeutic response.

According to another aspect of the invention, an embodiment of the invention includes a method of treating a patient with fecal incontinence by applying energy to an anal sphincter to produce a therapeutic response.

According to yet another aspect of the invention, an embodiment of the invention includes a method of ablating tissue in a gall bladder by applying energy to the gall bladder to produce a therapeutic response.

In embodiments, the applied energy is ultrasound, and the amount of applied energy may be adjusted as desired. In other embodiments, an endoscope with a working channel is inserted into the body, and an ultrasound device is advanced through the working channel to the desired body portion. In yet other embodiments, the energy is applied via an ultrasound device. In still other embodiments, the energy is applied below the surface of the desired body portion. In another embodiment, the energy from the ultrasound device is focusing on the desired body portion. In yet another embodiment, the ultrasound device is positioned outside of the patient.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE EMBODIMENTS

Reference will now be made in detail to the present exemplary embodiments of the invention, examples of which are illustrated in the accompanying drawings. Wherever possible, the same reference numbers will be used throughout the drawings to refer to the same or like parts.

Energy such as ultrasound may be used to minimize the invasiveness of medical procedures to treat the body. Ultrasound can provide therapeutic responses to internal and external body portions without the need for cuts or incisions, and can act on tissue below the surface of the tissue or organ.

An ultrasound device that may be used in medical procedures is an ultrasound transducer or ultrasound focusing device disclosed in U.S. patent application Publication No. 2001/0031922 A1 to Weng et al. ("Weng"), the complete disclosure of which is incorporated herein by reference. Weng discloses using the ultrasound transducer for imaging and therapeutic purposes. For imaging purposes (for example, imaging internal human organs for diagnostic purposes) ultrasound in the frequency range of 2-20 MHz and/or an intensity of less that 0.1 watts per square centimeter is used. For therapeutic purposes, a much more high intensity ultrasound above 200 watts per square centimeter is used. Such high intensity ultrasound can raise the temperature of a desired tissue region to above 60 degrees Celsius in a few seconds.

Figure 1A:
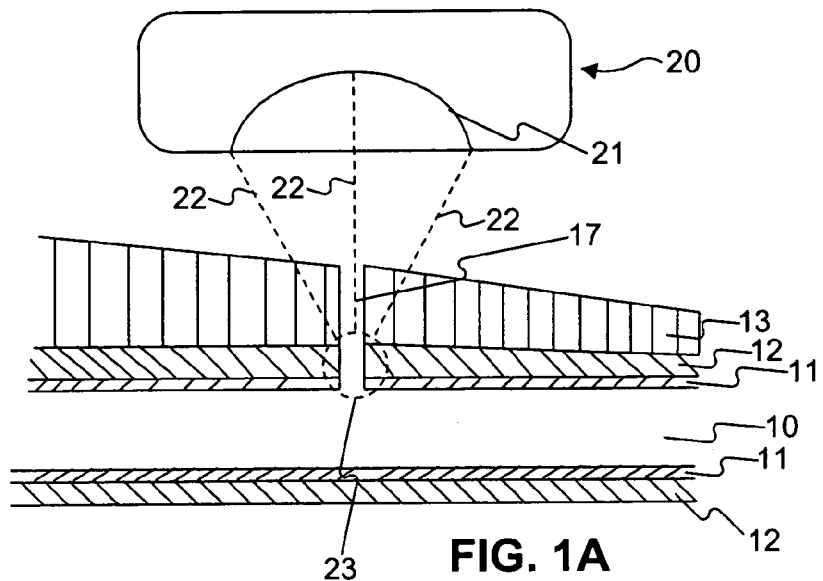
FIG. 1A is a schematic view of an exemplary method of sealing vascular punctures.
Figure 1B:
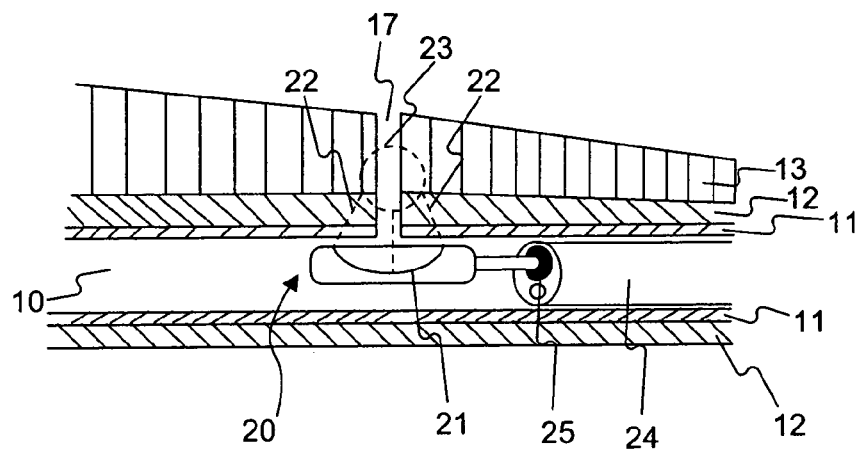
FIG. 1B is a schematic view of another exemplary method of sealing vascular punctures.
Figure 1C:
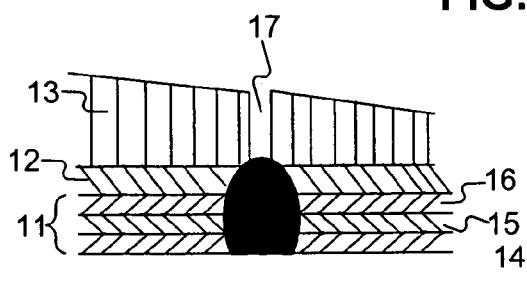
FIG. 1C is a schematic view of a sealed vascular puncture resulting from the method shown in FIG. 1A.
Figure 1D:
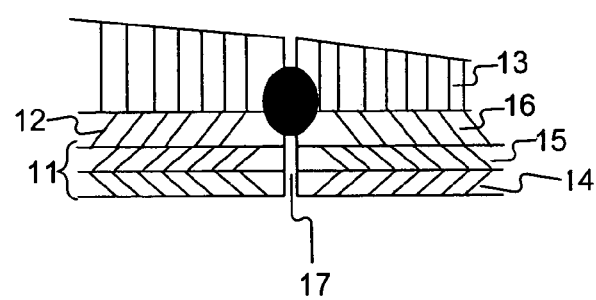
FIG. 1D is a schematic view of a sealed vascular puncture resulting from the method shown in FIG. 1B.

One application for ultrasound is vascular sealing. Accordingly, a method of effecting vascular sealing without the insertion of foreign objects into the blood vessel puncture includes the use of ultrasound. FIGS. 1A-1D show the sealing of blood vessel punctures through the use of ultrasound 22, for example, by using the ultrasound focusing device 20 disclosed in Weng. To seal a blood vessel puncture 17 using ultrasound 22, ultrasound focusing device 20 is positioned proximate the blood vessel puncture 17. If the blood vessel puncture 17 is close enough to the surface of the skin, the ultrasound focusing device 20 may be placed outside of the body, as shown in FIG. 1A. If, however, the blood vessel puncture 17 is further in the body, for example close to an internal organ, a catheter 24 with a lumen 25 may be advanced through the cardiovascular system until it is proximate the blood vessel puncture 17, and then the ultrasound focusing device 20 is advanced through the lumen 25 of catheter 24 until it also is proximate the blood vessel puncture 17, as shown in FIG. 1B. At this point, the ultrasound focusing device 20 is preferably past the distal end of catheter 24. Ultrasound focusing device 20 then is positioned, configured, and calibrated such that the focal point 23 of the ultrasound 22 will be centered on the portion of the puncture 17 to be sealed. Methods of positioning, configuring, and calibrating the ultrasound focusing device 20, for example by adjusting an ultrasound array 21, are disclosed in Weng, the disclosure of which is incorporated by reference herein. The geometry and/or positioning of the ultrasound focusing device 20 can be adjusted so that the focal point 23 will be at a proper distance from the ultrasound focusing device 20, particularly if the desired focal point 23 is below the surface of the subcutaneous tissue 13 and/or blood vessel wall 11, as shown in FIGS. 1B and 1D. However, the desired focal point may also be on a surface of the tissue 13 or blood vessel wall 11, as shown in FIGS. 1A and 1C. The geometry and positioning of the ultrasound focusing device 20 can also be adjusted such that it will only act on a specified volume of tissue at and/or surrounding the focal point 23. Both the focal point 23 and the volume of tissue to be energized can be adjusted at any time during the procedure, for example, prior to, during, and/or subsequent to the application of energy to various tissue portions (i.e. any or all of the subcutaneous tissue 13, vascular sheath 12, adventitia 16, media layer 15, or intima layer 14) via the ultrasound focusing device 20.

Once properly positioned, the ultrasound focusing device 20 is activated such that energy is applied via ultrasound 22 to the tissue at the desired focal point 23. In this case, because the object of the procedure is to seal the blood vessel puncture 17, the amount of energy supplied by the ultrasound focusing device 20 to the desired focal point 23 is rapidly and significantly increased such that the temperature of the tissue at the focal point 23 rises very rapidly. For example, energy in the frequency range of 10 kHz to 300 GHz may be applied to the tissue for between 1 and 10 seconds such that the temperature of the tissue at the focal point 23 rises to over 60 degrees Celsius. For medical reasons, the frequency may be above 25 kHz. The rapid rise in temperature causes the tissue at the focal point 23, for example the adventitia 16 and the vascular sheath 12, to denature so that the puncture 17 is closed, and then fuse so that the puncture 17 is sealed. In effect, the tissue is cauterized so as to effect sealing, as shown in FIGS. 1C and 1D. In addition, the heat generated at the focal point 23 may cause thrombosis and/or coagulate the blood around the focal point 23 and/or in the vascular puncture 17, which may further facilitating the vascular sealing. However, such thrombosis and/or coagulation is not necessary, and sometimes even undesired as it may lead to additional complications, especially if such thrombosis and coagulation spreads to outside of the vascular puncture 17 and into the blood vessel 10. When the puncture 17 has been sufficiently closed and sealed, the application of energy to the tissue at the focal point 23 is terminated and the ultrasound focusing device 20 is either moved to another body portion, or removed from the body completely.

Figure 2A:
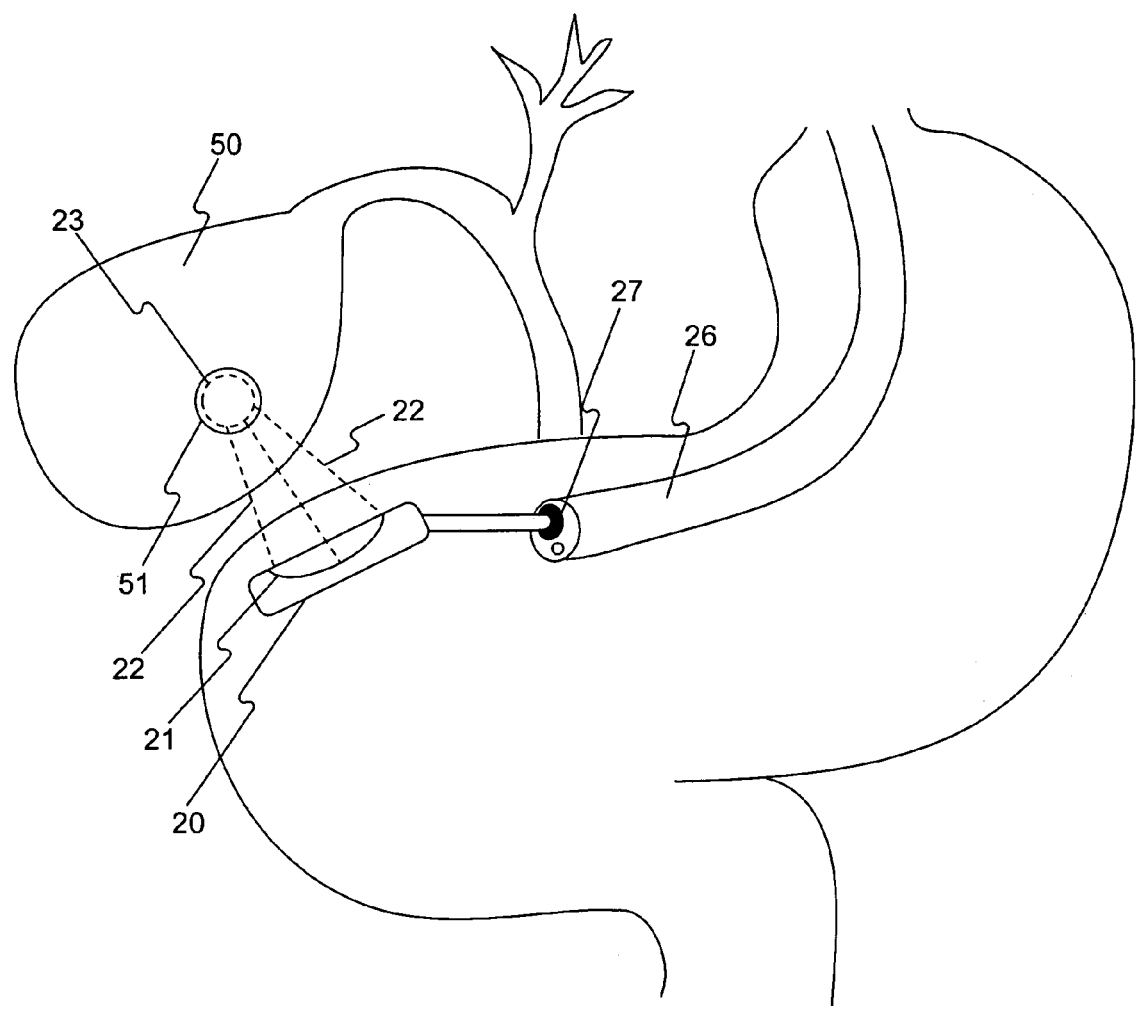
FIG. 2A is a schematic view of an exemplary method of ablating a gall bladder.
Figure 2B:
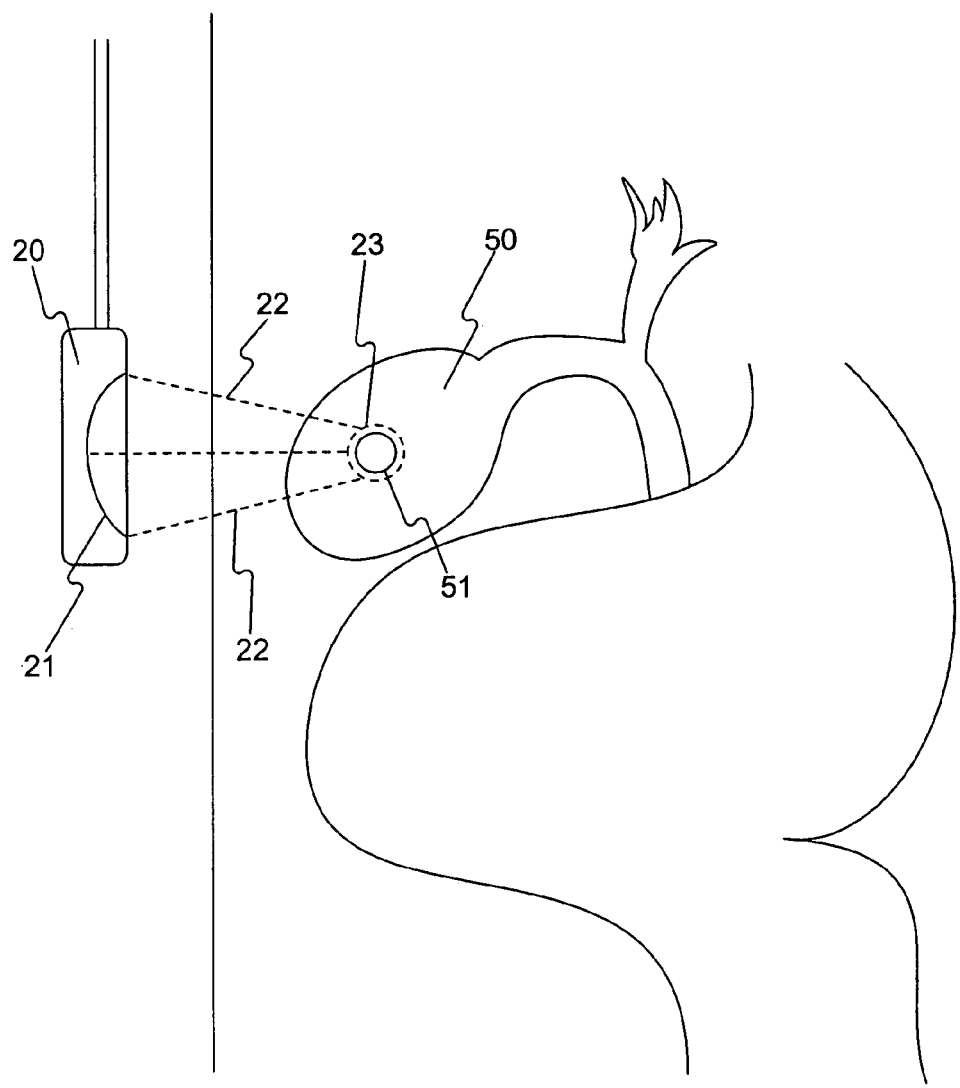
FIG. 2B is a schematic view of another exemplary method of ablating a gall bladder.

FIGS. 2A and 2B disclose exemplary methods of ablating a portion of the gall bladder 50 during inside-out surgery through the use of ultrasound 22, for example, by using the ultrasound focusing device 20 disclosed in Weng. Inside-out surgery is the performance of surgery from the inside of the body portion (e.g. without making any cuts or incisions in that body portion). To ablate a portion of the gall bladder 50, for example a lesion 51 in the gall bladder 50, an ultrasound focusing device 20 is positioned proximate the gall bladder 50. For example, an endoscope 26 with a working channel 27 is advanced through the gastrointestinal system until it is proximate the gall bladder 50. The endoscope 26 is advanced through the gastrointestinal tract due to the tract's close proximity to the gall bladder 50, however, advancing an endoscope or other access device through any body lumen that provides access to the gall bladder 50 is also contemplated. Then, the ultrasound focusing device 20 is advanced through the working channel 27 of the endoscope 26 until it is distal the end of endoscope 26 and proximate the gall bladder 50, as shown in FIG. 2A. In another example, however, the ultrasound focusing device 20 may be positioned external to the body such that it is proximate the gall bladder 50, as shown in FIG. 2B. The ultrasound focusing device 20 is then positioned, configured, and calibrated such that the focal point 23 of the ultrasound 22 will be centered on the portion of the gall bladder 50 with the lesion 51, for example, using methods disclosed in Weng for the ultrasound array 21. The geometry and or positioning of the ultrasound focusing device 20 can be adjusted so that the focal point 23 will be at a proper distance from the ultrasound focusing device 20, as in this case the lesion 51 is either inside the gall bladder 50 or on the gall bladder's surface. The geometry and positioning of the ultrasound focusing device 20 can also be adjusted such that it will only act on a specified volume of tissue at and/or surrounding the focal point 23 (i.e. will only act on the lesion 51 or other undesirable portion of the gall bladder 50, or a portion of the undesirable tissue or lesion 51, and not significantly affect other healthy tissue portions). Both the focal point 23 and the volume of tissue can be adjusted at any time during the procedure, for example, prior to, during, and/or subsequent to the application of energy.

Once properly positioned, the ultrasound focusing device 20 is activated such that energy is applied via ultrasound 22 to the lesion 51 or at least a portion of the lesion 51. In this case, because the object of the procedure is to ablate the lesion 51, the amount of energy supplied by the ultrasound focusing device 20 to the lesion 51 at the desired focal point 23 is rapidly and significantly increased such that the temperature of the lesion tissue 51 rises very rapidly. For example, energy in the frequency range of 10 kHz to 300 GHz may be applied to the tissue for between 1 and 10 seconds such that the temperature of the tissue at the focal point 23 rise to over 60 degrees Celsius. For medical reasons, the frequency may be above 25 kHz. The rapid rise in temperature causes almost immediate tissue ablation and/or tissue necrosis of at least a portion of the lesion 51, and effectively destroys the tissue. If the entire lesion 51 has not been destroyed at this point, the position and/or volume of the focal point 23 of the ultrasound focusing device 20 can be shifted around, for example by adjusting the ultrasound array 21, so as to destroy other portions of the lesion for which destruction is desired. Such shifting of the position and/or volume of the focal point 23 may occur while the energy is still being applied, or during periods where energy is not applied. In some cases, however, destruction of the entire lesion 51 may not be desired, as destroying all of the lesion 51 may also cause the destruction of healthy tissue. During this procedure, the surrounding healthy tissue should be relatively unaffected as only the energy from the ultrasound 22 converging at the focal point 23 should have enough magnitude to affect the tissue in any significant way. After the desired tissue has been destroyed, the ultrasound focusing device 20 and endoscope 26 can be removed. During the healing process, the healthy gall bladder tissue 50 should absorb the destroyed tissue and/or remnants of the lesion 51.

Figure 3A:
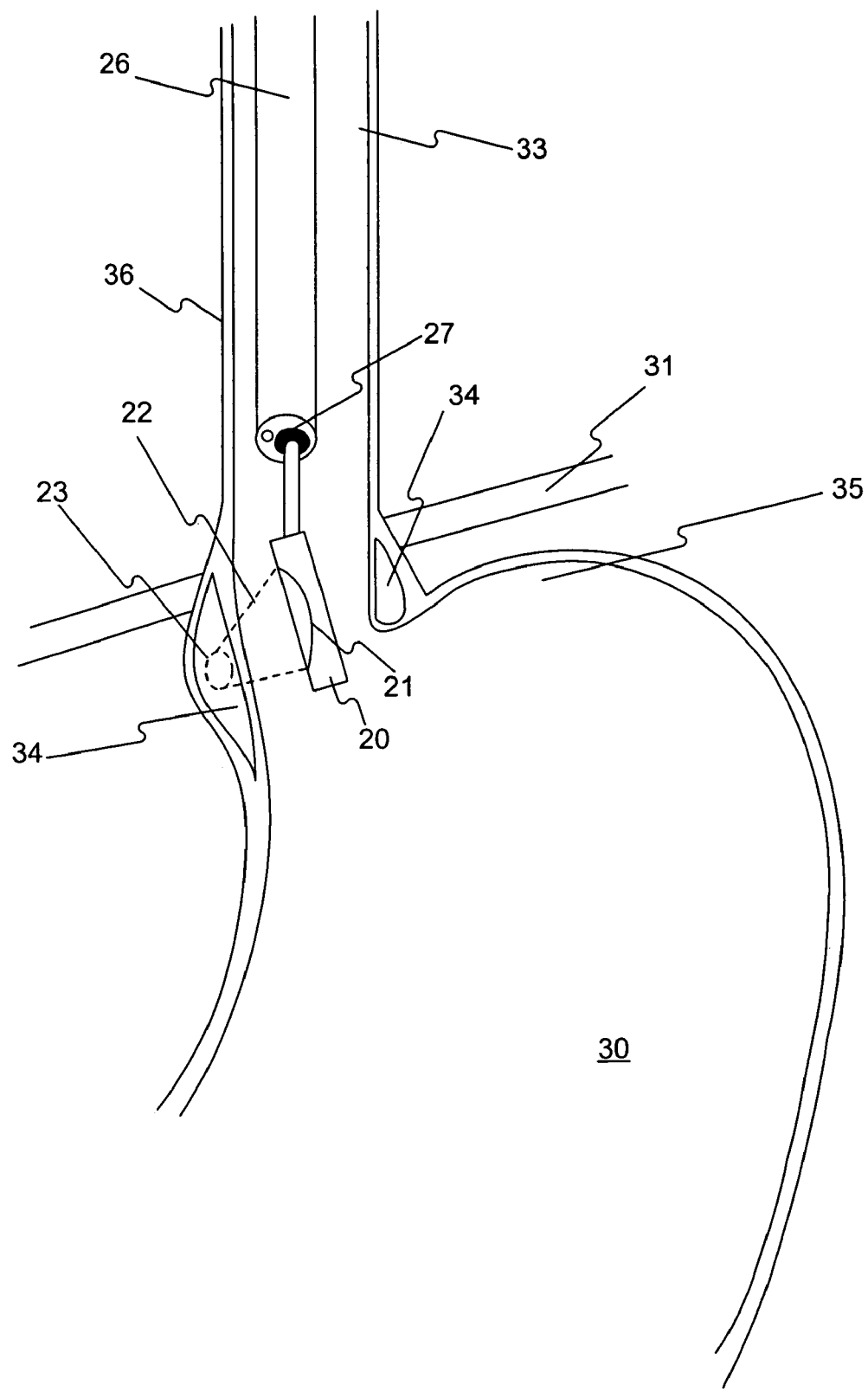
FIG. 3A is a schematic view of an exemplary method of treating GERD.
Figure 3B:
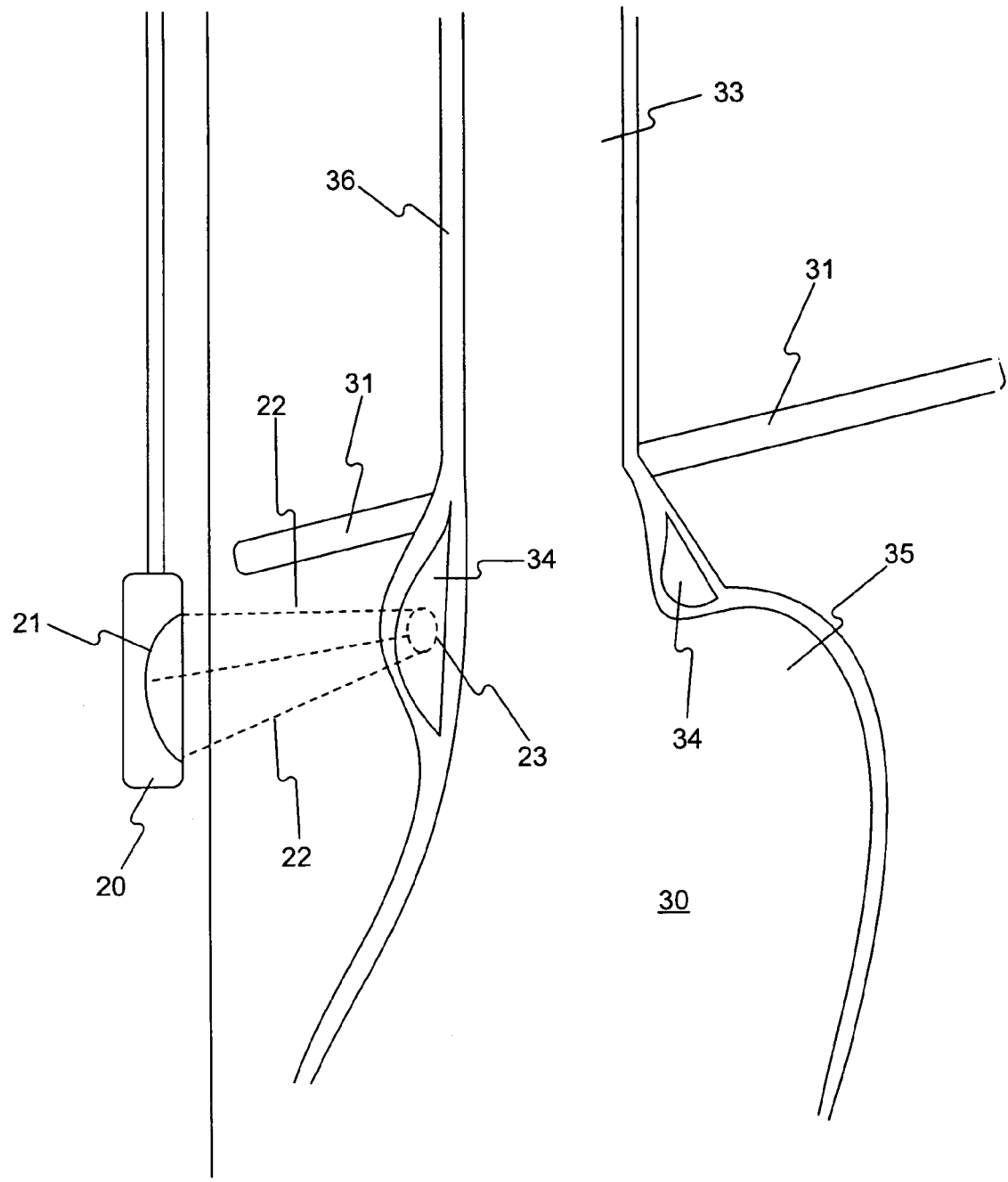
FIG. 3B is a schematic view of another exemplary method of treating GERD.

FIGS. 3A and 3B depict exemplary methods of treating gastrointestinal reflux disease (GERD) through the use of ultrasound 22, for example, by using the ultrasound focusing device 20 disclosed in Weng. For example, an endoscope 26 may be advanced through the esophagus 33 until its distal end is proximate the LES 34. The ultrasound focusing device 20 is then advanced through the working channel 27 of the endoscope 26 until it also is proximate the LES 34, as shown in FIG. 3A. In another example, however, the ultrasound focusing device 20 may be positioned external to the body such that it is proximate the LES 34, as shown in FIG. 3B. The ultrasound focusing device 20 is then adjusted, for example as described above in other ultrasound applications, such that the focal point 23 of the device 20 is targeted at the desired tissue portion, for example by adjusting the ultrasound array 21 using methods disclosed above. In this case, ultrasound focusing device 20 can be used to induce hyperplasia in the esophageal wall 36, and particularly to the LES 34, to help close off the esophageal opening into the stomach and/or to accommodate the proper placement of the diaphragm 31 relative to the LES 34. Furthermore, the ultrasound focusing device can also be used to heat the collagen in the esophagus 33, specifically the esophageal wall 36, which will cause the lumen of the esophagus 33 to shrink. This will also help close off the esophageal opening into the stomach and/or accommodate the proper placement of the diaphragm 31 relative to the LES 34.

For hyperplasia, once the ultrasound focusing device 20, for example the ultrasound array 21, has been positioned and/or adjusted, ultrasound energy is applied to the tissue portion in sufficient amounts to cause injury to the desired tissue portion. The surrounding tissue should be relatively unaffected as only the energy from the ultrasound 22 converging at the focal point 23 should have enough magnitude to affect the desired tissue in any significant way. After sufficiently injuring desired tissue portions such that a healing response will result in hyperplasia or other tissue growth, the ultrasound focusing device 20 is either moved to another body portion, or completely removed from the body. The injured tissue and the surrounding tissue of esophageal wall 36 and LES 34 then invokes its natural healing response and repairs the damaged tissue. In injuring the tissue, hyperplasia often results where new tissue is formed in and/or around the injured tissue, thus adding bulk and mass to the tissue portion. In addition, by controlling the amount of ultrasound 22 applied to the targeted tissue area, the amount of tissue injury, and hence the amount of tissue that will be added by the hyperplasia process, can be controlled. The amount and/or duration of energy applied may also take into account other factors, such as the characteristics of the tissue being affected, distance of the desired focal point 23 from the ultrasound focusing device 20, distance of the desired focal point 23 from the surface of the tissue, and/or acceptable risk that overexposing the tissue will not result in the amount of hyperplasia desired.

For heating the collagen in the esophageal wall 36, once the ultrasound focusing device 20, for example the ultrasound array 21, has been positioned and/or adjusted, ultrasound energy is applied to the desired collagen portions in sufficient amounts to heat the collagen to the temperature at which it breaks down and/or denatures. This denaturing and/or breaking down will cause the collagen to shrink, and hence cause the lumen of the esophagus 33 to shrink as well. The surrounding tissue should be relatively unaffected as only the energy from the ultrasound 22 converging at the focal point 23 should have enough magnitude to affect the desired tissue in any significant way. After sufficiently heating the collagen portions such that they denature and/or break down, the ultrasound focusing device 20 is either moved to another body portion, or completely removed from the body. The heated collagen portions shrink, also causing shrinkage to the lumen of the esophagus 33. In addition, by controlling the amount of ultrasound 22 applied to the targeted collagen portions, the amount of heat applied to the collagen, and hence the amount of shrinkage that the lumen of the esophagus 33 will undergo, can be controlled. The amount and/or duration of energy applied may also take into account other factors, such as the. characteristics of the collagen being affected, distance of the desired focal point 23 from the ultrasound focusing device 20, distance of the desired focal point 23 from the surface of the collagen, and/or acceptable risk that overexposing the collagen will destroy it.

Figure 4B:
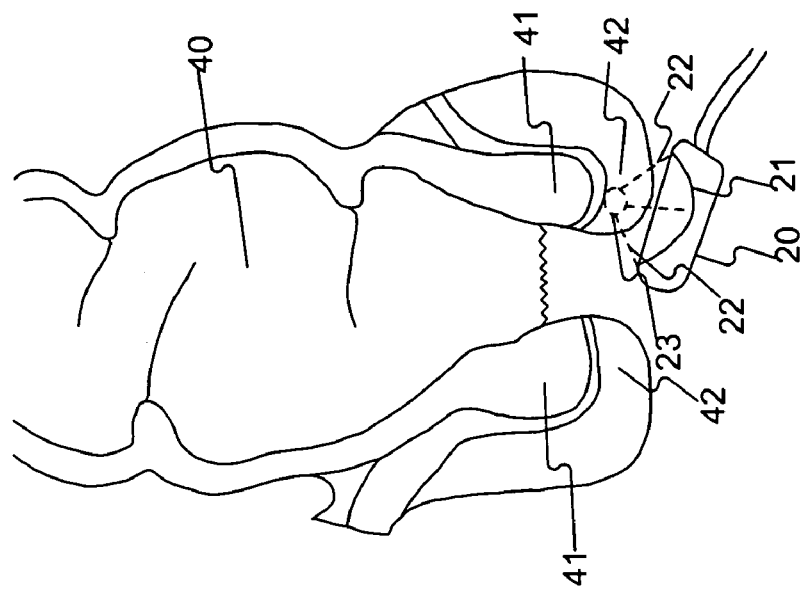
FIG. 4B is a schematic view of another exemplary method of treating fecal incontinence.
Figure 4A:
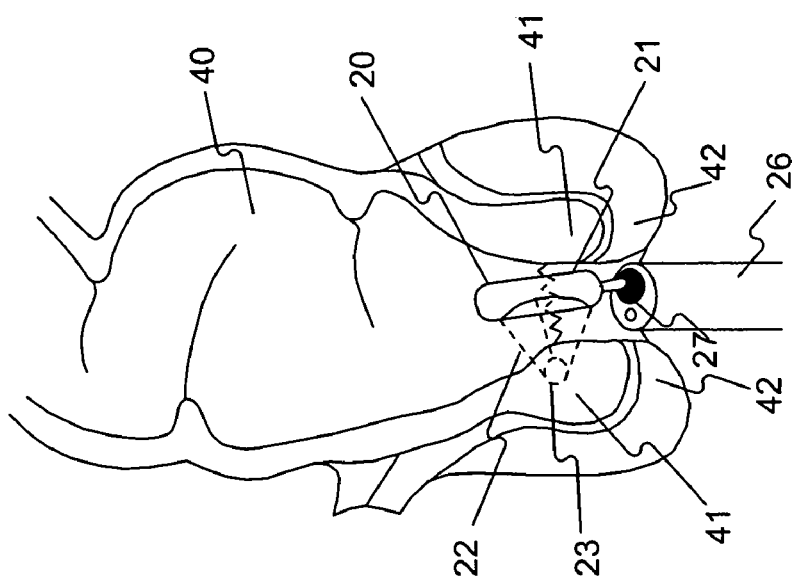
FIG. 4A is a schematic view of an exemplary method of treating fecal incontinence.

FIGS. 4A-4B disclose exemplary methods of treating fecal incontinence through the use of ultrasound 22, for example, by using the ultrasound focusing device 20 disclosed in Weng. For example, an ultrasound focusing device can be used to rebuild the anal sphincter, specifically by inducing hyperplasia. To do this, the ultrasound focusing device 20 is positioned such that its distal end is proximate either the internal anal sphincter 41, as shown in FIG. 4A, or external anal sphincter 42, as shown in FIG. 4B. As the external anal sphincter 42 is close to the surface of the skin, and the internal anal sphincter 41 is also relatively close to the surface of the skin, the ultrasound focusing device can be positioned outside the body, as shown in FIG. 4B. However, the ultrasound focusing device 20 may also be positioned just inside the body in the lower colon 40 for treating either the internal anal sphincter 41 or external anal sphincter 42, as shown in FIG. 4A. In the latter case, an endoscope 26 first may be positioned with its distal end 40 proximate the sphincter 41, 42. The ultrasound focusing device then may be advanced through the working channel 27 of the endoscope 26 until it is proximate the anal sphincter 41, 42. In all cases, once properly positioned, the ultrasound focusing device 20 is then adjusted, for example as in the procedures disclosed in this application for adjusting the ultrasound array 21, such that the focal point 23 of the device 20 is targeted at the desired tissue portion. In this case, the desired tissue portion is a part of the anal sphincter 41, 42 which, when hyperplasia is induced, will close the gap in the anal sphincter 41, 42. The focal area 23 of the ultrasound focusing device 20 will also be adjusted so that the ultrasound 22 will be directed to the proper volume of tissue at and/or surrounding the focal point 23.

Once the ultrasound focusing device 20 has been adjusted, energy is applied via ultrasound 22 to the tissue portion in sufficient amounts to only cause injury to the desired tissue portion, for example using one of the methods disclosed above. The surrounding tissue should be relatively unaffected as only the energy from the ultrasound 22 converging at the focal point 23 should have enough magnitude to affect the desired tissue in any significant way. After sufficiently injuring desired tissue portions such that a healing response will result in hyperplasia or other tissue growth, the ultrasound focusing device is moved. The injured tissue and the surrounding tissue, here the internal anal sphincter 41 or external anal sphincter 42, then invokes its natural healing response and repairs the damaged tissue. In doing so, hyperplasia often results where new tissue is formed in and/or around the injured tissue, thus adding bulk and mass to the tissue portion. In addition, by controlling the amount of ultrasound 22 applied to the targeted tissue area, the amount of tissue injury, and hence the amount of bulk and mass that will be added to the tissue by the hyperplasia process, can be controlled. The amount and/or duration of energy applied may also take into account other factors, such as the characteristics of the tissue being affected, distance of the desired focal point 23 from the ultrasound focusing device 20, distance of the desired focal point 23 from the surface of the tissue, and/or acceptable risk that overexposing the tissue will not result in the amount of hyperplasia desired.

Figure 5B:
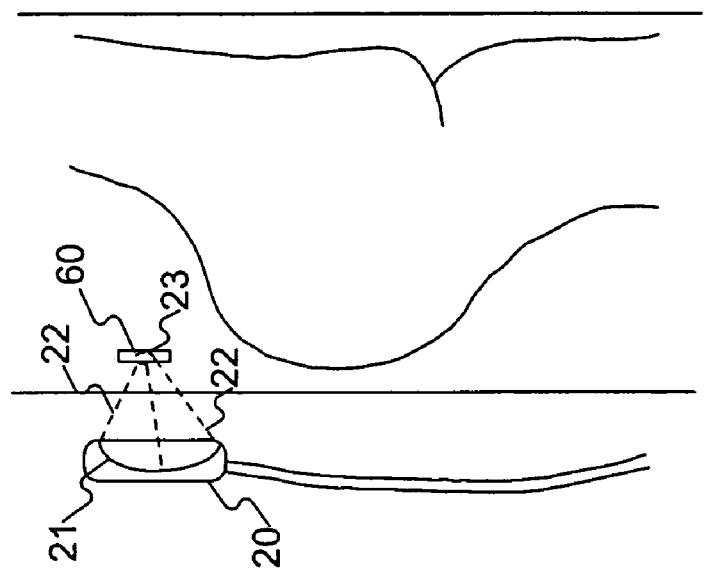
FIG. 5B is. a schematic view of another method of activating a mechanical implant.
Figure 5A:
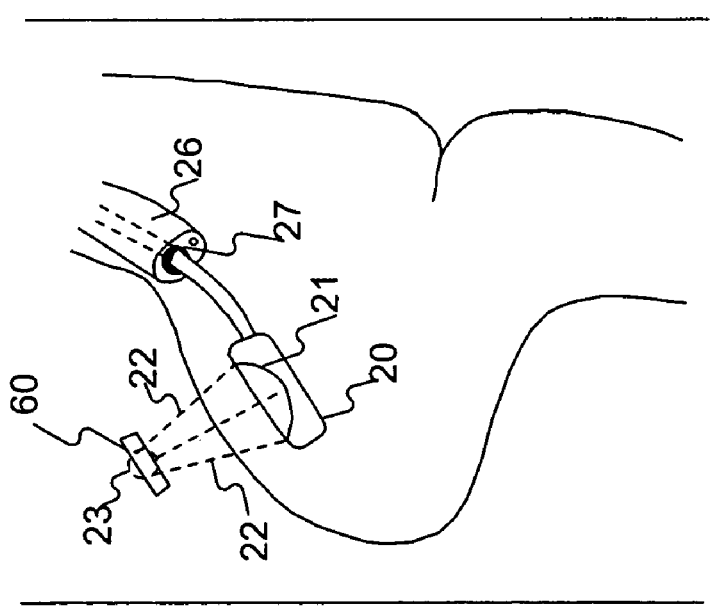
FIG. 5A is a schematic view of a method of activating a mechanical implant.

FIGS. 5A and 5B depict exemplary methods of activating a mechanical implant 60. Once a mechanical device 60 has been implanted in the body, it may require activation. Accordingly, an ultrasound focusing device 20 may be positioned proximate the mechanical implant 60 using any of the methods disclosed above. For example, the ultrasound focusing device 20 may be advanced through the working channel 27 of an endoscope 26 disposed in the gastrointestinal tract, as shown in FIG. 5A, or it may be positioned external to the body proximate the mechanical implant 60, as shown in FIG. 5B. Once properly positioned, the ultrasound focusing device 20 is then adjusted, for example as in the procedures disclosed in this application for adjusting the ultrasound array 21, such that the focal point 23 of the device 20 is targeted at the mechanical implant 60 or the desired portion of the mechanical implant 60. In this case, the desired implant portion is a part of the implant 60 which requires activation. The focal area 23 of the ultrasound focusing device 20 will also be adjusted so that the ultrasound 22 will be directed to the proper volume of the implant 60 and/or tissue at and/or surrounding the focal point 23.

Once the ultrasound focusing device 20 has been adjusted, energy is applied via ultrasound 22 to the implant 60 in sufficient amounts to activate the implant 60, for example using one of the methods disclosed above. The surrounding tissue should be relatively unaffected as only the energy from the ultrasound 22 converging at the focal point 23 should have enough magnitude to affect the implant 60 and/or the tissue in any significant way. After sufficiently activating the implant 60, the ultrasound focusing device is moved. The implant 60 then performs its allotted function. In addition, by controlling the amount of ultrasound 22 applied to the implant 60, the amount of activation, and hence the amount of treatment by the implant, can be controlled. The amount and/or duration of energy applied may also take into account other factors, such as the characteristics of the implant 60 and/or tissue being affected, distance of the desired focal point 23 from the ultrasound focusing device 20, distance of the desired focal point 23 from the surface of the tissue, and/or acceptable risk that overexposing the implant 60 will not result in the desired activation and/or treatment. The activation may only occur while energy is being applied to implant 60 via ultrasound, or may continue even after application of energy has stopped. In other embodiments, a mechanical device such as a surgical instrument placed in the body to perform a treatment, as opposed to an implant in the body, may be activated through ultrasound.

In various embodiments, the delivery of ultrasonic energy to treat various internal organs or tissue is exemplary. Other types of energy and/or energy delivery devices may be used, including radio frequency, microwaves, lasers, electromagnetics, cryogenic fluids, heat, mechanical devices, or other energy delivery systems known in the art.

In various embodiments, the application of energy, for example via ultrasound 22, can be to either the surface or internal portions of any vessel, organ, and/or other body portion. Using any of the methods disclosed above, the application of energy via ultrasound 22 may be used to treat tumors, lesions, cancerous tissue, non-cancerous tissue, benign tissue growths, and other desirable or undesirable tissue.

In various embodiments, steps in above described methods can be interchanged and substituted into any of the other above described methods. For example, in treating GERD, it may be desirable to cause tissue necrosis in a portion of the esophagus 33, LES 34, fundus wall 35, or esophageal wall 36. Accordingly, some of the steps in the method of ablating tissue in the gall bladder may be used to cause tissue necrosis in any of the aforementioned portions. In another example, in treating fecal incontinence, it may be desirable to cause tissue necrosis in a portion of the anal sphincter 41, 42. Accordingly, some of the steps in the method of ablating tissue in the gall bladder 50 may be used to cause tissue necrosis in a portion of the anal sphincter 41, 42. In yet another example, it may be desirable to increase the mass in a section of the gall bladder 50. Accordingly, some of the steps in the method of increasing tissue mass in either the LES 34 or anal sphincter 41, 42 may be used to increase mass in a section of the gall bladder 50. In addition, any of the steps in any of the above-described methods may be repeated as necessary, for example, to treat multiple sections of the esophagus 33, ablate multiple lesions 51, or close multiple punctures 17. Also, certain steps in any of the above-described methods may be deleted as desired or necessary. For example, devices other than an endoscope may be used to deliver the ultrasound focusing device 20.

In various embodiments, the use and/or treatment of specific organs and/or body parts in describing each of the above methods is exemplary. Other organs and/or body parts may be treated or used for access to treated tissue or organs, as desired. For example, the method for ablating tissue is not be limited to the gall bladder 50, as other internal organs (e.g., the liver, lung, kidney, pancreas, prostate, bladder, uterus, or brain) from which tissue removal is required may also have tissue removed by ablation substantially as described above. In another example, the method for bulking up tissue is not be limited to portions of the gastrointestinal tract, as other organs, vessels, or tissue in the body that requires an increase in bulk or mass may also be treated using the methods described above. In yet another example, the method for sealing is not limited to blood vessels 10, as other tissue, organs, or walls which has a puncture 17, whether artificial or natural, that requires sealing may be sealed using the method as described above.

In various embodiments, the use of ultrasound to produce a therapeutic response in the body and the use of ultrasound for imaging purposes may be combined. For example, an ultrasound device may be used to both view the desired body portion and also to direct the ultrasound focusing device in the desired body portion. Any other method of viewing the desired body portion and/or directing the ultrasound focusing device is also contemplated.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating a patient with gastrointestinal reflux disease comprising:
   applying energy from a device to an esophageal sphincter to produce a therapeutic response,
   wherein the therapeutic response includes effecting sufficient injury to the esophageal sphincter to cause hyperplasia,
   wherein the entire device is positioned outside of an esophagus of the patient during the step of applying energy.

2. The method of claim 1, wherein the applied energy is ultrasound.

3. The method of claim 1, further comprising adjusting the amount of energy applied to the esophageal sphincter.

4. The method of claim 1, wherein the therapeutic response includes bulking tissue of the esophageal sphincter.

5. The method of claim 1, wherein the energy is applied to a portion of the esophageal sphincter below a surface of the esophageal sphincter.

6. The method of claim 1, wherein the device is an ultrasound device, and further comprising focusing the energy from the ultrasound device on a portion of the esophageal sphincter.

7. The method of claim 6, wherein the energy is focused below a surface of the esophageal sphincter.

8. The method of claim 1, wherein the entire device is positioned outside of the patient during the step of applying energy.

9. A method of treating a patient with gastrointestinal reflux disease comprising:

applying energy to an esophageal sphincter to produce a therapeutic response, wherein the therapeutic response includes effecting sufficient injury to the esophageal sphincter to cause hyperplasia, wherein the energy is applied to the esophageal sphincter via an ultrasound device, and further comprising focusing the energy from the ultrasound device on a portion of the esophageal sphincter, wherein the ultrasound device is positioned outside of the patient.

10. A method of treating a patient with gastrointestinal reflux disease comprising:

applying energy from a device to an esophageal sphincter to produce a therapeutic response, wherein the energy is applied to a portion of the esophageal sphincter below a surface of the esophageal sphincter, wherein the entire device is positioned outside of an esophagus of the patient during the step of applying energy.

11. The method of claim 10, wherein the applied energy is ultrasound.

12. The method of claim 10, further comprising adjusting the amount of energy applied to the esophageal sphincter.

13. The method of claim 10, wherein the therapeutic response is effecting sufficient injury to the esophageal sphincter to cause hyperplasia.

14. The method of claim 13, wherein the therapeutic response includes bulking tissue of the esophageal sphincter.

15. The method of claim 10, wherein the therapeutic response includes bulking tissue of the esophageal sphincter.

16. The method of claim 10, wherein the device is an ultrasound device, and further comprising focusing the energy from the ultrasound device on a portion of the esophageal sphincter.

17. The method of claim 10, wherein the entire device is positioned outside of the patient during the step of applying energy.

18. A method of treating a patient with gastrointestinal reflux disease comprising:

applying energy to an esophageal sphincter to produce a therapeutic response, wherein the energy is applied to a portion of the esophageal sphincter below a surface of the esophageal sphincter, wherein the energy is applied to the esophageal sphincter via an ultrasound device, and further comprising focusing the energy from the ultrasound device on a portion of the esophageal sphincter, wherein the ultrasound device is positioned outside of the patient.

19. A method of treating a patient with fecal incontinence comprising:

applying energy from a device to an anal sphincter to produce a therapeutic response, wherein the therapeutic response is effecting sufficient injury to the anal sphincter to cause hyperplasia, wherein the entire device is positioned outside of an anus of the patient during the step of applying energy.

20. The method of claim 19, wherein the applied energy is ultrasound.

21. The method of claim 19, further comprising adjusting the amount of energy applied to the anal sphincter.

22. The method of claim 19, wherein the therapeutic response includes bulking tissue of the anal sphincter.

23. The method of claim 19, wherein the energy is applied to a portion of the anal sphincter below a surface of the anal sphincter.

24. The method of claim 19, wherein the device is an ultrasound device and further comprising focusing the energy from the ultrasound device on a portion of the anal sphincter.

25. The method of claim 24, wherein the energy is focused below a surface of the anal sphincter.

26. The method of claim 19, wherein the entire device is positioned outside of the patient during the step of applying energy.

27. A method of treating a patient with fecal incontinence comprising:

applying energy to an anal sphincter to produce a therapeutic response, wherein the energy is applied to the anal sphincter via an ultrasound device, the method further comprising focusing the energy from the ultrasound device on a portion of the anal sphincter, and positioning the ultrasound device outside the patient, wherein the therapeutic response is effecting sufficient injury to the anal sphincter to cause hyperplasia.

* * * * *